United States Patent
Koka et al.

(10) Patent No.: US 10,668,284 B2
(45) Date of Patent: Jun. 2, 2020

(54) SYSTEMS AND METHODS FOR DETERMINING A STAPEDIUS REFLEX THRESHOLD BASED ON ELECTRO-ACOUSTIC STIMULATION

(71) Applicant: Advanced Bionics AG, Staefa (CH)

(72) Inventors: Kanthaiah Koka, Valencia, CA (US); Leonid M. Litvak, Los Angeles, CA (US)

(73) Assignee: Advanced Bionics AG, Staefa (CH)

(*) Notice: Subject to any disclaimer, the term of this patent is extended or adjusted under 35 U.S.C. 154(b) by 142 days.

(21) Appl. No.: 15/885,553

(22) Filed: Jan. 31, 2018

(65) Prior Publication Data
US 2018/0229035 A1 Aug. 16, 2018

Related U.S. Application Data

(60) Provisional application No. 62/460,072, filed on Feb. 16, 2017.

(51) Int. Cl.
*A61N 1/36* (2006.01)
*A61N 1/05* (2006.01)
(Continued)

(52) U.S. Cl.
CPC ....... *A61N 1/36039* (2017.08); *A61N 1/0541* (2013.01); *A61N 1/37229* (2013.01); *A61N 1/37235* (2013.01)

(58) Field of Classification Search
CPC ...... H04R 25/00; H04R 25/30; H04R 25/606; H04R 2225/67; H04R 29/00; H04R 25/70;
(Continued)

(56) References Cited

U.S. PATENT DOCUMENTS

| 8,086,319 B2 | 12/2011 | Van Dijk |
| 2012/0300964 A1 | 11/2012 | Ku et al. |

(Continued)

FOREIGN PATENT DOCUMENTS

| WO | 2012/056427 | 5/2012 |
| WO | 2013/142843 | 9/2013 |
| WO | 2017/182931 | 10/2017 |

*Primary Examiner* — Jon Eric C Morales
(74) *Attorney, Agent, or Firm* — ALG Intellectual Property, LLC

(57) ABSTRACT

A stapedius reflex threshold determination system is communicatively coupled with a loudspeaker and a cochlear implant implanted within a patient. The system identifies a baseline evoked response level associated with a baseline acoustic stimulation level too low to trigger a stapedius reflex within the patient. The system directs an electro-acoustic stimulation event to be applied to the patient, including electrical stimulation applied by the cochlear implant at a particular electrical stimulation level and acoustic stimulation applied by the loudspeaker at the baseline acoustic stimulation level. The system determines an evoked response level associated with the applied acoustic stimulation and detects that the stapedius reflex is triggered by determining that the evoked response level is at least a predetermined threshold amount lower than the baseline evoked response level. In response to this detection, the system may determine a stapedius reflex threshold of the patient based on the particular electrical stimulation level.

20 Claims, 11 Drawing Sheets

(51) Int. Cl.
*A61B 5/12* (2006.01)
*A61B 5/04* (2006.01)
*A61N 1/372* (2006.01)

(58) Field of Classification Search
CPC .... H04R 29/008; H04R 2225/43; A61B 5/00; A61B 5/4851; A61B 5/742; A61B 5/7475; A61B 5/125; A61B 5/12; A61B 5/123; A61N 1/36; A61N 1/36036; A61N 1/0541; A61N 1/36039
USPC .......................... 600/340, 504, 552, 554, 25
See application file for complete search history.

(56) References Cited

U.S. PATENT DOCUMENTS

2013/0006328 A1 1/2013 Bouchataoui et al.
2018/0015287 A1* 1/2018 Heasman ........... A61N 1/36036

* cited by examiner

US 10,668,284 B2

SYSTEMS AND METHODS FOR DETERMINING A STAPEDIUS REFLEX THRESHOLD BASED ON ELECTRO-ACOUSTIC STIMULATION

RELATED APPLICATIONS

The present application claims priority under 35 U.S.C. § 119(e) to U.S. Provisional Patent Application No. 62/460,072, filed on Feb. 16, 2017, and entitled "Systems and Methods for Determining a Stapedius Reflex Threshold Based on Electro-acoustic Stimulation," the contents of which are hereby incorporated by reference in their entirety.

BACKGROUND INFORMATION

Cochlear implant systems (also known as cochlear prostheses) have been developed to help overcome certain types of hearing loss. For example, a cochlear implant system may include a cochlear implant (i.e., a stimulator implanted within a patient) that bypasses hair cells in the patient's cochlea by applying electrical stimulation directly to auditory nerve fibers by way of an array of electrodes implanted in the cochlea. Direct stimulation of the auditory nerve fibers in this way leads to the perception of sound in the patient's brain and at least partial restoration of hearing function. Additionally, for cochlear implant patients who retain at least some amount of residual hearing, certain cochlear implant systems may be employed that leverage and help preserve the residual hearing. Such cochlear implant systems may be known as electro-acoustic stimulation ("EAS") systems, and, for example, may use a loudspeaker to apply, in conjunction with the electrical stimulation applied by the cochlear implant, acoustic stimulation to functional hair cells in the cochlea.

When a cochlear implant is initially implanted in a patient (e.g., as part of a regular cochlear implant system or an EAS system), as well as during follow-up tests and checkups thereafter, it may be desirable to fit the cochlear implant to the patient. Such "fitting" may include adjustment (e.g., within a sound processor that directs and/or controls the cochlear implant) of a base amplitude or intensity of various stimuli generated by the cochlear implant from the factory settings or default values to values that are most effective and comfortable for the patient. For example, the intensity or amplitude and/or duration of the individual stimulation applications (i.e., continuous bursts of stimulation pulses) provided by the cochlear implant system may be mapped to an appropriate dynamic audio range so that the appropriate "loudness" of sensed audio signals is perceived. Ultimately, by properly fitting a cochlear implant (i.e., fitting the cochlear implant system) to a patient, it may be ensured that loud sounds are perceived by the patient as loud, but not painfully loud, and that soft sounds are perceived by the patient at soft levels, but not such soft levels that the sounds are not perceivable at all.

One aspect of fitting a cochlear implant to a particular patient is determining at least one most comfortable level ("MCL"), also known as a "most comfortable current level" or an "M level." An MCL refers to a stimulation current level applied by a cochlear implant system at which the patient is most comfortable. MCLs typically vary from patient to patient and from electrode channel to electrode channel in a multichannel cochlear implant.

MCLs are typically determined based on subjective feedback provided by cochlear implant patients. For example, a clinician may present various stimuli to a patient and then analyze subjective feedback provided by the patient as to how the stimuli were perceived. Subjective feedback may take the form of verbal feedback (e.g., in the case of adults), or non-verbal feedback (e.g., in the case of certain children). Unfortunately, relying on subjective feedback in this manner is difficult, particularly for those patients who may have never heard sound before and/or who have never heard electrically-generated "sound." For young children, the problem is further exacerbated by short attention spans and/or difficulty in understanding instructions and concepts (e.g., high and low pitch, softer and louder, same and different, etc.). Moreover, certain patients such as infants and/or patients with certain disabilities may be unable to provide any subjective feedback.

Consequently, it may be desirable to determine MCLs of certain cochlear implant patients by way of an objective technique, rather than by means of the subjective feedback. To this end, it is known that the MCLs of most patients tend to be highly correlated with (e.g., in many cases, substantially equal to or slightly offset from) stapedius reflex thresholds ("SRTs") of the patients, which may be determined objectively (i.e., without requiring subjective feedback). An SRT of a particular patient is the threshold loudness level at which the patient's brain triggers a stapedius reflex, a natural hearing protection mechanism in humans whereby the stapedius muscle of the middle ear involuntarily contracts in response to uncomfortably or dangerously loud sounds to apply tension to the ossicles of the inner ear and thereby reduce the amplitude of vibrations reaching the cochlea. As useful as the determination of an SRT can be for fitting the patient with the cochlear implant, however, current techniques for determining SRTs leave room for improvement. For example, current SRT determination techniques typically require additional instrumentation (e.g., middle ear analyzers, extra electrodes beyond the electrodes used to provide the electrical stimulation, etc.) to be inserted into the ear. Such additional instrumentation may be inconvenient, risky, painful, and otherwise detrimental to the patient and/or the clinicians and other medical personnel working with the patient.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

Figure 7:
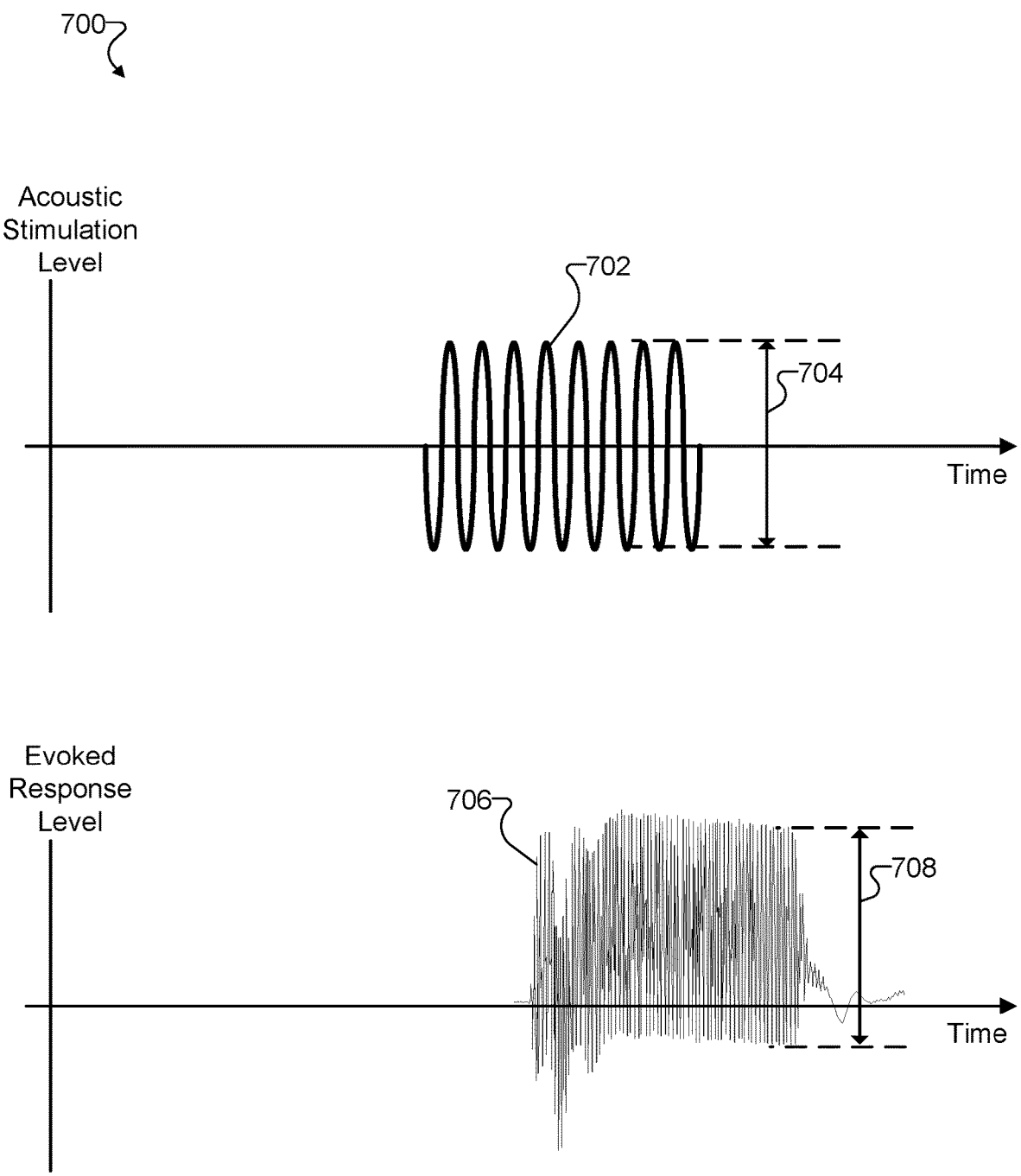

FIG. 7 illustrates exemplary waveforms depicting an evoked response that occurs within the patient in response to acoustic stimulation being applied to the patient according to principles described herein.

Figure 8:
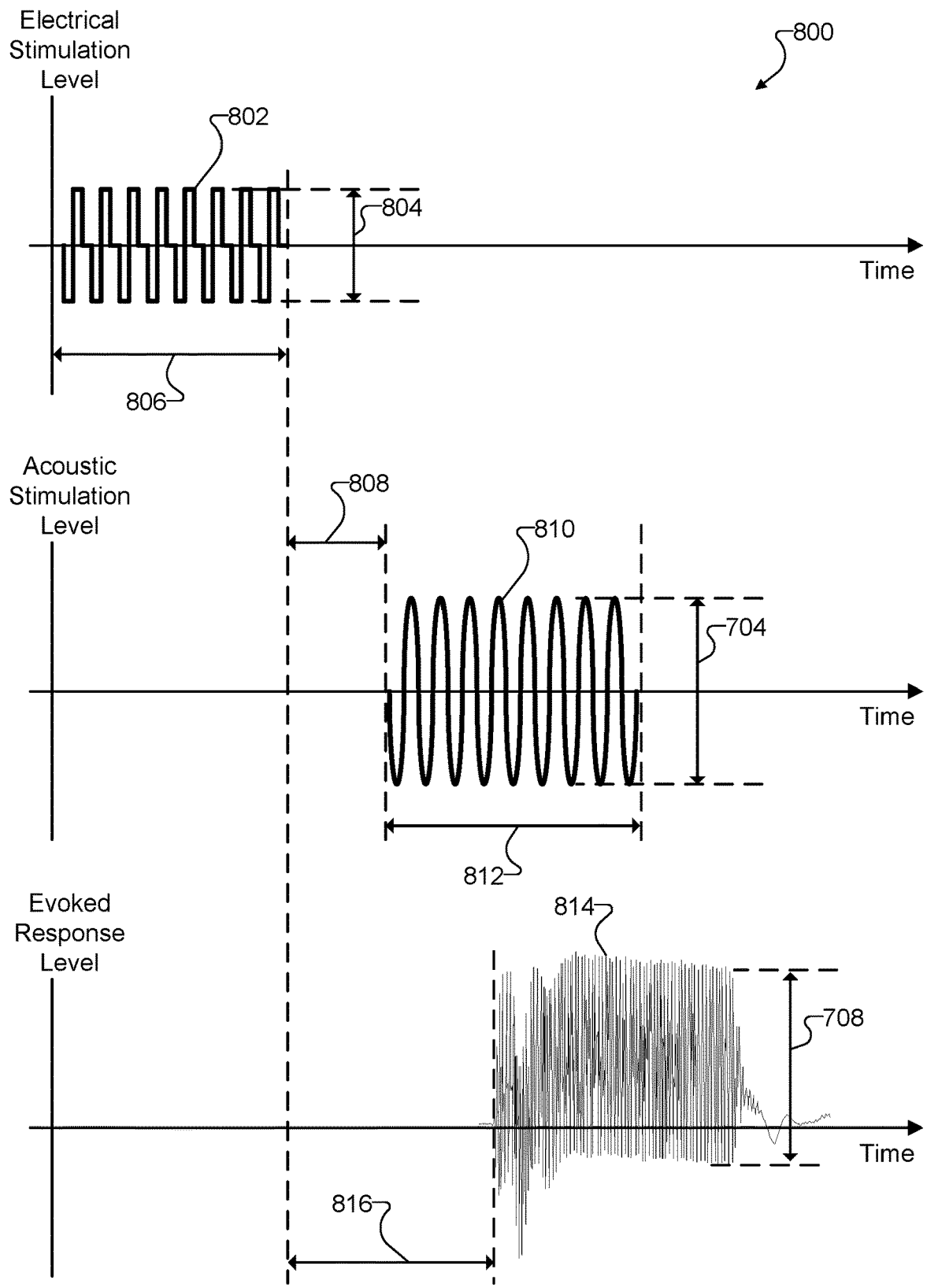
Figure 9:
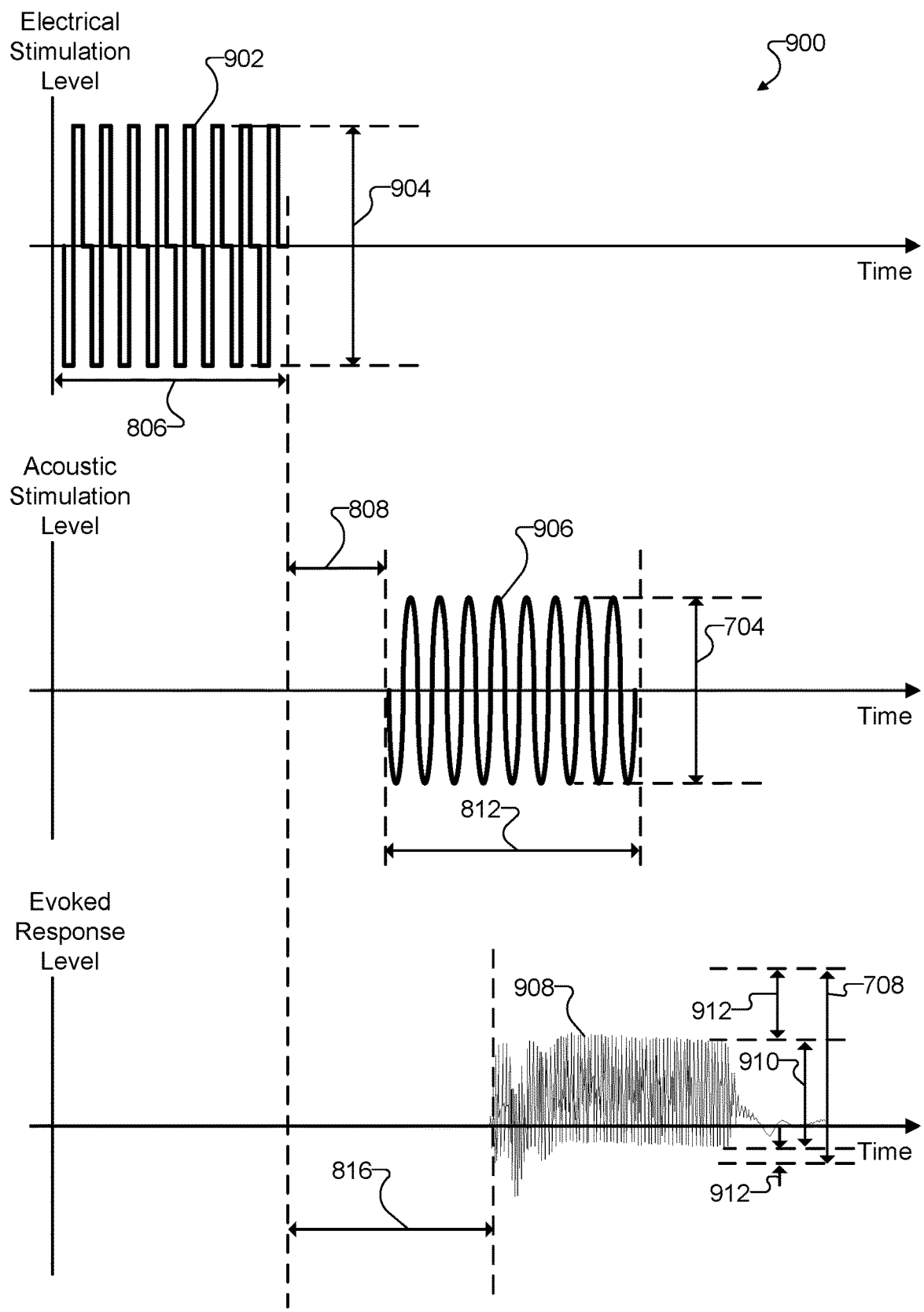
Figure 10:
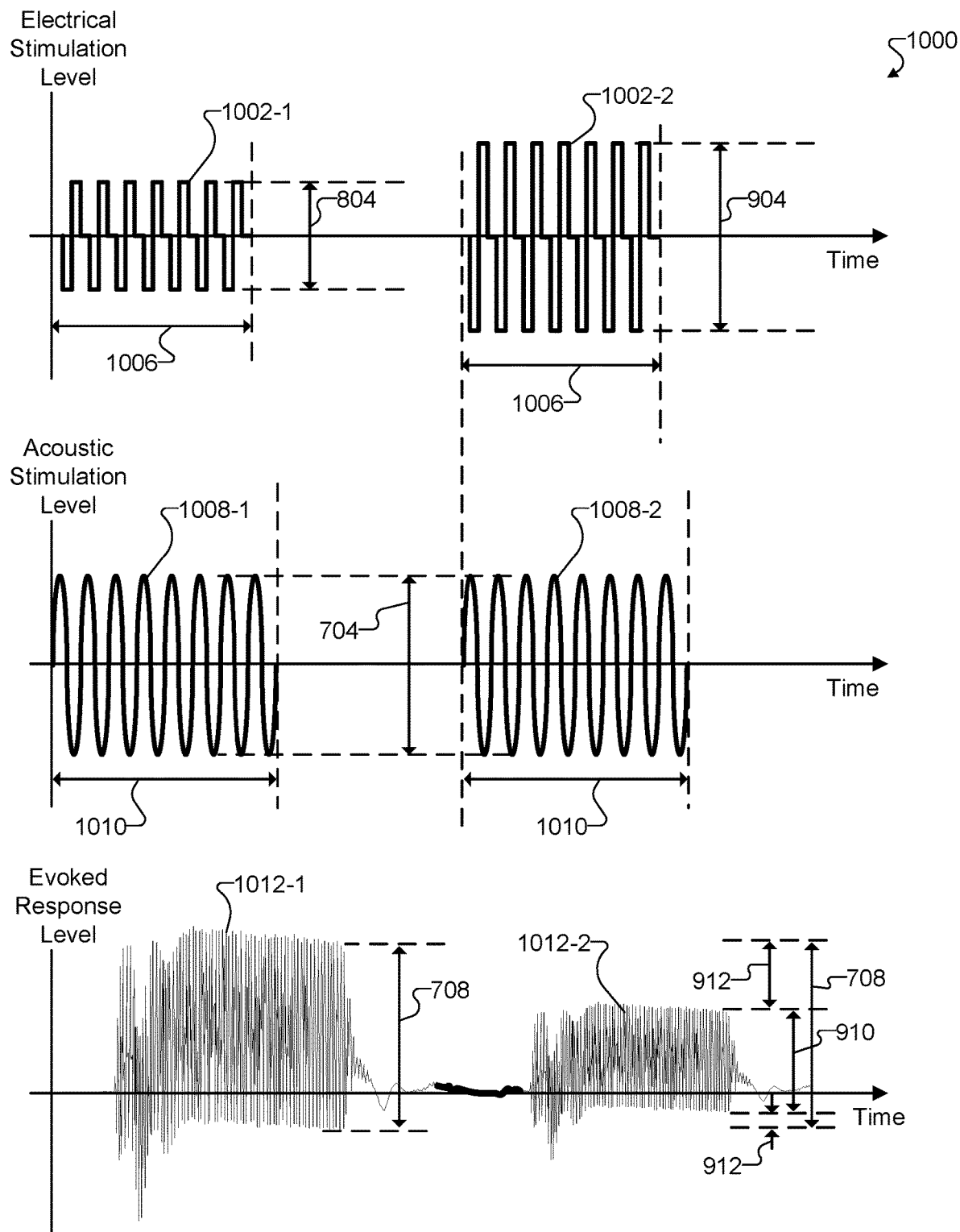

FIGS. 8-10 illustrate exemplary waveforms depicting various electro-acoustic stimulation events applied to the patient and respective evoked responses that occur within the patient in response to acoustic stimulation included within the various electro-acoustic stimulation events according to principles described herein.

Figure 11:
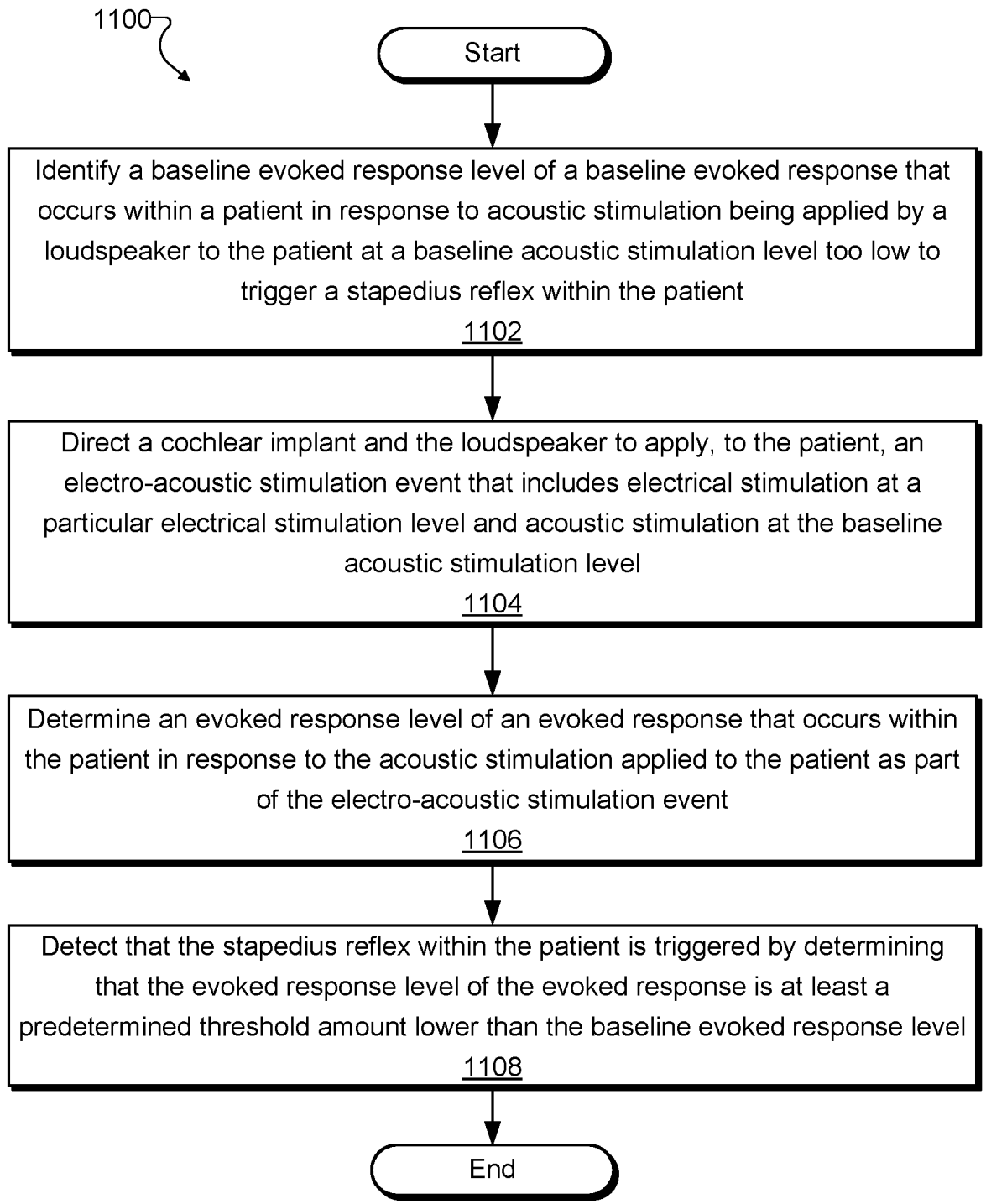

FIG. 11 illustrates an exemplary method for determining an SRT based on electro-acoustic stimulation according to principles described herein.

DETAILED DESCRIPTION

Systems and methods for determining a stapedius reflex threshold ("SRT") based on electro-acoustic stimulation are described herein. For instance, one exemplary system may include a loudspeaker associated with (e.g., positioned and configured to generate sound to be heard by) a patient with residual hearing, a cochlear implant implanted within the patient, and an SRT determination system communicatively coupled with the loudspeaker and the cochlear implant. The SRT determination system may direct the cochlear implant and the loudspeaker to apply electro-acoustic stimulation (e.g., electrical stimulation applied by the cochlear implant and acoustic stimulation applied by the loudspeaker) and may determine the SRT based on a detection and/or analysis of various evoked responses (e.g., electrocochleographic evoked potentials, acoustic brainstem responses, etc.) that occur in response to and/or are affected by the applied electro-acoustic stimulation.

More specifically, the SRT determination system may identify a baseline evoked response level (e.g., a voltage level) of a baseline evoked response that occurs within the patient in response to acoustic stimulation (e.g., a sound such as a tone or the like) being applied by the loudspeaker to the patient at a baseline acoustic stimulation level. For example, the baseline acoustic stimulation level may be too low to trigger a stapedius reflex within the patient and, as such, may predictably evoke a consistent response at a particular evoked response level (i.e., the baseline evoked response level). The baseline evoked response level may be identified in various ways, as will be described in more detail below.

The SRT determination system may further direct the cochlear implant and the loudspeaker to apply one or more electro-acoustic stimulation events to the patient. For example, each electro-acoustic stimulation event may include both electrical stimulation applied by the cochlear implant at an electrical stimulation level and acoustic stimulation applied by the loudspeaker at an acoustic stimulation level. In some implementations, the electrical stimulation levels of successive applications of the electrical stimulation may gradually escalate (e.g., until reaching a particular electrical stimulation level large enough to trigger the stapedius reflex), while the acoustic stimulation levels of successive applications of the acoustic stimulation may remain consistent at the baseline acoustic stimulation level that is too low to trigger the stapedius reflex. As such, evoked responses that occur in response to the acoustic stimulation applied at the baseline acoustic stimulation level may be consistent (i.e., at the identified baseline evoked response level described above) until the electrical stimulation grows large enough to trigger the stapedius reflex, at which point the evoked response may reveal the triggering of the stapedius reflex by reflecting an effect of the electrical stimulation, as will be described below.

In conjunction with directing the cochlear implant and the loudspeaker to apply each electro-acoustic stimulation event to the patient, the SRT determination system may determine respective evoked response levels of respective evoked responses that occur within the patient in response to the acoustic stimulation applied to the patient as part of the electro-acoustic stimulation events. For example, in conjunction with the application of the electro-acoustic stimulation event in which the electrical stimulation has escalated to reach the particular electrical stimulation level large enough to trigger the stapedius reflex, the SRT determination system may determine an evoked response level of a particular evoked response that has been affected by the stapedius reflex. Accordingly, the SRT determination system may detect that the stapedius reflex is triggered by determining that the evoked response level of the particular evoked response has been affected by the stapedius reflex (e.g., by determining that the evoked response level is at least a predetermined threshold amount lower than the baseline evoked response level).

In response to this detection that the stapedius reflex within the patient is triggered, and based on the particular electrical stimulation level at which the stapedius reflex has been triggered, the SRT determination system may determine an SRT of the patient. Additionally, once the SRT determination system determines the SRT, the SRT determination system may further determine a most comfortable level ("MCL") of the patient based on the determined SRT, and may provide data representative of the MCL to facilitate fitting the cochlear implant to the patient.

By determining an SRT (e.g., as well as an MCL) based on electro-acoustic stimulation in this way, the methods and systems described herein may provide various benefits to clinicians and patients. For example, for patients who are unable to provide adequate subjective feedback needed to allow clinicians to properly fit a cochlear implant to the patients, these systems and methods for objectively determining both the SRT of the patients and, based on the SRT, the MCL of the patients, may allow the cochlear implants to be properly fitted to the patients even without any subjective feedback from the patients. Accordingly, such patients may benefit by obtaining properly fitted cochlear implants that allow the patients to hear at more comfortable and appropriate loudness levels than if the cochlear implants were not properly fitted. Additionally, even for patients who are capable of providing subjective feedback, the methods and systems for determining an SRT based on electro-acoustic stimulation described herein may provide clinicians with an objective data point with regard to the patient's MCL that may be valuable in various ways during the fitting sessions to facilitate the fitting process and ensure the patient gets the best fit possible.

Moreover, by determining the SRT based on electro-acoustic stimulation in accordance with the systems and methods described herein, clinicians and patients may benefit in comparison to other techniques for determining an MCL using a detected SRT. For example, by determining the SRT using the systems and methods herein, various instruments such as middle ear analyzers, additional electrodes, and/or other instrumentation used to determine the SRT in other techniques may be avoided. Thus, by determining the SRT using only instruments that are part of a cochlear implant system (e.g., an electro-acoustic stimulation ("EAS") system) and/or are external to the patient and part of the fitting process anyway (e.g., a programming device communicatively coupled to the cochlear implant system), the clinician and/or the patient may enjoy an easier, faster, more convenient, less risky, and/or less painful fitting session experience. For example, the time it takes for a stapedius reflex threshold to be determined may be reduced, which may be especially beneficial for certain types of patients (e.g., pediatric patients) with short attention spans. Additionally, patient safety may increase by preventing the patient from being over-stimulated during a fitting session.

Various embodiments will now be described in more detail with reference to the figures. The disclosed systems and methods may provide one or more of the benefits mentioned above and/or various additional and/or alternative benefits that will be made apparent herein.

Figure 1:
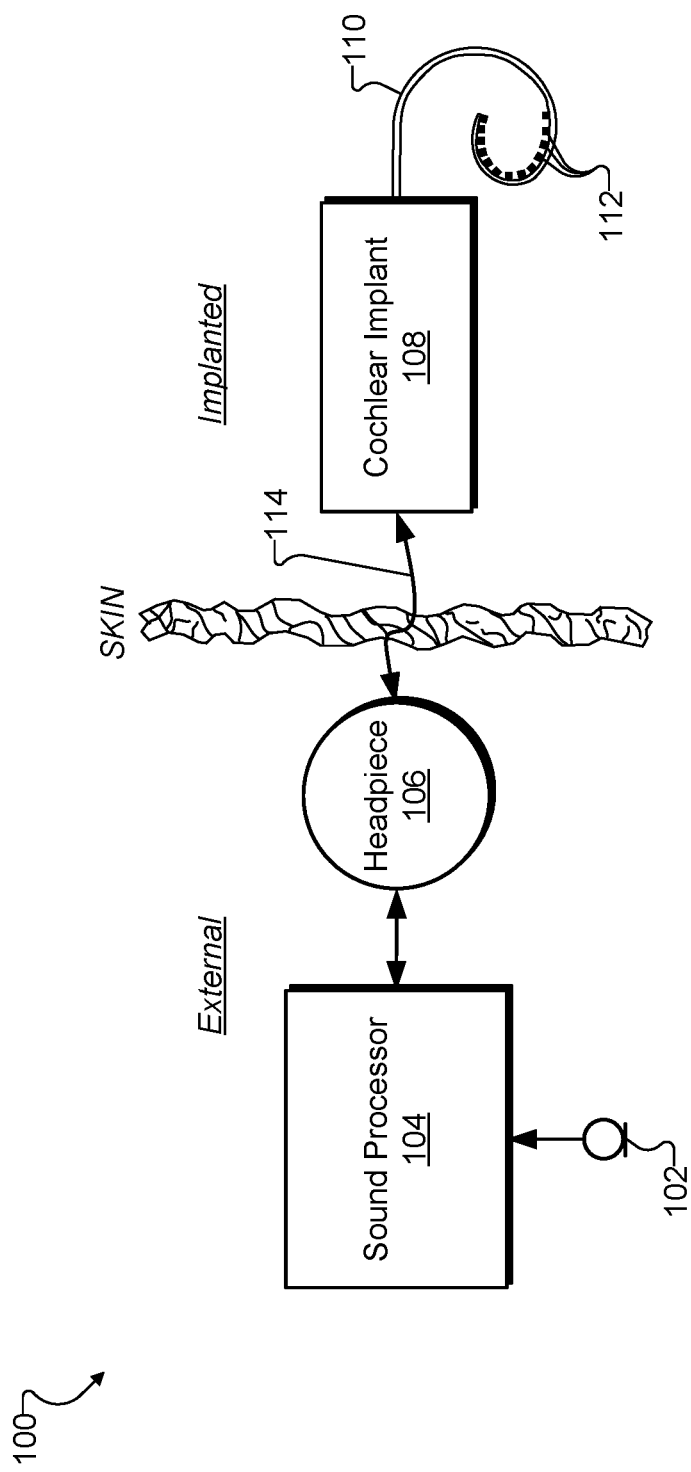
FIG. 1 illustrates an exemplary cochlear implant system that may facilitate determining a stapedius reflex threshold ("SRT") based on electro-acoustic stimulation according to principles described herein.

FIG. 1 shows an exemplary cochlear implant system 100. As will be described in more detail below, cochlear implant system 100 may facilitate determining an SRT based on electro-acoustic stimulation by including or being used in conjunction with an SRT determination system. As shown, cochlear implant system 100 may include various components configured to be located external to a cochlear implant patient including, but not limited to, a microphone 102, a sound processor 104, and a headpiece 106. Cochlear implant system 100 may further include various components configured to be implanted within the patient including, but not limited to, a cochlear implant 108 (also referred to as an implantable cochlear stimulator) and a lead 110 (also referred to as an intracochlear electrode array) with a plurality of electrodes 112 disposed thereon. In certain examples, additional or alternative components may be included within cochlear implant system 100 as may serve a particular implementation. For example, as will be described in more detail below, if cochlear implant system 100 is an EAS system, a loudspeaker (not explicitly shown in FIG. 1) may be communicatively coupled with sound processor 104. It will be understood that in certain implementations (e.g., "fully implantable" implementations), one or more of the components described and illustrated as being external to the patient may alternatively be implanted within the patient. The components shown in FIG. 1 will now be described in more detail.

Microphone 102 may be configured to detect audio signals presented to the patient. Microphone 102 may be implemented in any suitable manner. For example, microphone 102 may include a microphone such as a T-MIC™ microphone from Advanced Bionics. Microphone 102 may be associated with a particular ear of the patient such as by being located in a vicinity of the particular ear (e.g., within the concha of the ear near the entrance to the ear canal). In some examples, microphone 102 may be held within the concha of the ear near the entrance of the ear canal by a boom or stalk that is attached to an ear hook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone or microphones as may serve a particular implementation.

Sound processor 104 (e.g., a sound processor included within sound processor 104) may be configured to direct cochlear implant 108 to generate and apply electrical stimulation (also referred to herein as "stimulation current") representative of one or more audio signals (e.g., one or more audio signals detected by microphone 102, directed to be applied by an SRT determination system, input by way of an auxiliary audio input port, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. While, for the sake of simplicity, electrical stimulation will be described herein as being applied to one or both of the *cochleae* of a patient, it will be understood that stimulation current may also be applied to other suitable nuclei in the auditory pathway. To this end, sound processor 104 may process the one or more audio signals in accordance with a selected sound processing strategy or program (i.e., a selected sound processing program) to generate appropriate stimulation parameters for controlling cochlear implant 108.

Sound processor 104 may include or be implemented by a behind-the-ear ("BTE") unit, a body worn device, and/or any other sound processing unit as may serve a particular implementation. In some examples, sound processor 104 may be implemented by an EAS sound processor included in an EAS system configured to provide electrical and acoustic stimulation to a patient (e.g., by way of cochlear implant 108 and a loudspeaker communicatively coupled to the EAS sound processor). Additionally, as will be described in more detail below, sound processor 104 may include at least one physical computing component (e.g., a processor, a memory, a storage device, etc.) implementing an SRT determination system for determining an SRT based on electro-acoustic stimulation.

In certain implementations, sound processor 104 may wirelessly transmit stimulation parameters (e.g., in the form of data words included in a forward telemetry sequence) and/or power signals to cochlear implant 108 by way of a wireless communication link 114 between headpiece 106 and cochlear implant 108. It will be understood that communication link 114 may include a bidirectional communication link and/or one or more dedicated unidirectional communication links. In some examples, sound processor 104 may execute and operate in accordance with a sound processing program that has been loaded into memory contained within sound processor 104.

Headpiece 106 may be communicatively coupled to sound processor 104 and may include an external antenna (e.g., a coil and/or one or more wireless communication components) configured to facilitate selective wireless coupling of sound processor 104 to cochlear implant 108. Headpiece 106 may additionally or alternatively be used to selectively and wirelessly couple any other external device to cochlear implant 108. To this end, headpiece 106 may be configured to be affixed to the patient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor 104 and cochlear implant 108 via communication link 114.

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of active implant or auditory prosthesis that may be implanted within a patient and configured to apply stimulation to one or more stimulation sites located along an auditory pathway of a patient.

In some examples, cochlear implant 108 may be configured to generate and apply electrical stimulation (e.g., representative of an audio signal detected by microphone 102 and processed by sound processor 104, representative of electrical stimulation at a particular electrical stimulation level as directed by an SRT determination system, etc.) in accordance with one or more stimulation parameters transmitted thereto by sound processor 104. Cochlear implant 108 may be further configured to apply the electrical stimulation to one or more stimulation sites within the patient via one or more electrodes 112 disposed along lead 110 (e.g., by way of one or more stimulation channels formed by electrodes 112). In some examples, cochlear implant 108 may include a plurality of independent current sources each associated with a channel defined by one or more of electrodes 112. In this manner, different stimulation current levels may be applied to multiple stimulation sites simultaneously (also referred to as "concurrently") by way of multiple electrodes 112.

Figure 2:
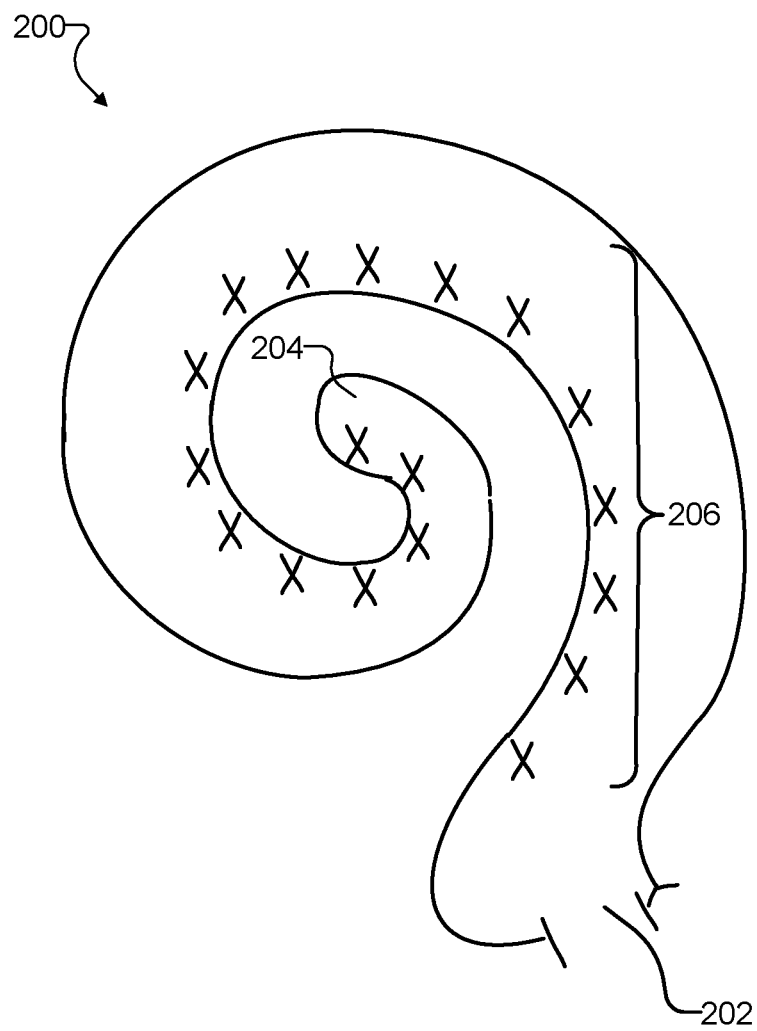
FIG. 2 illustrates a schematic structure of the human cochlea according to principles described herein.

FIG. 2 illustrates a schematic structure of a human cochlea 200 into which lead 110 may be inserted. As shown in FIG. 2, cochlea 200 is in the shape of a spiral beginning at a base 202 and ending at an apex 204. Within cochlea 200 resides auditory nerve tissue 206, which is denoted by Xs in FIG. 2. Auditory nerve tissue 206 is organized within cochlea 200 in a tonotopic manner. That is, relatively low frequencies are encoded at or near apex 204 of cochlea 200 (referred to as an "apical region") while relatively high frequencies are encoded at or near base 202 (referred to as a "basal region"). Hence, each location along the length of cochlea 200 corresponds to a different perceived frequency. Cochlear implant system 100 may therefore be configured to apply electrical stimulation to different locations within cochlea 200 (e.g., different locations along auditory nerve tissue 206) to provide a sensation of hearing to the patient. For example, when lead 110 is properly inserted into cochlea 200, each of electrodes 112 may be located at a different cochlear depth within cochlea 200 (e.g., at a different part of auditory nerve tissue 206) such that stimulation current applied to one electrode 112 may cause the patient to perceive a different frequency than the same stimulation current applied to a different electrode 112 (e.g., an electrode 112 located at a different part of auditory nerve tissue 206 within cochlea 200).

Figure 3:
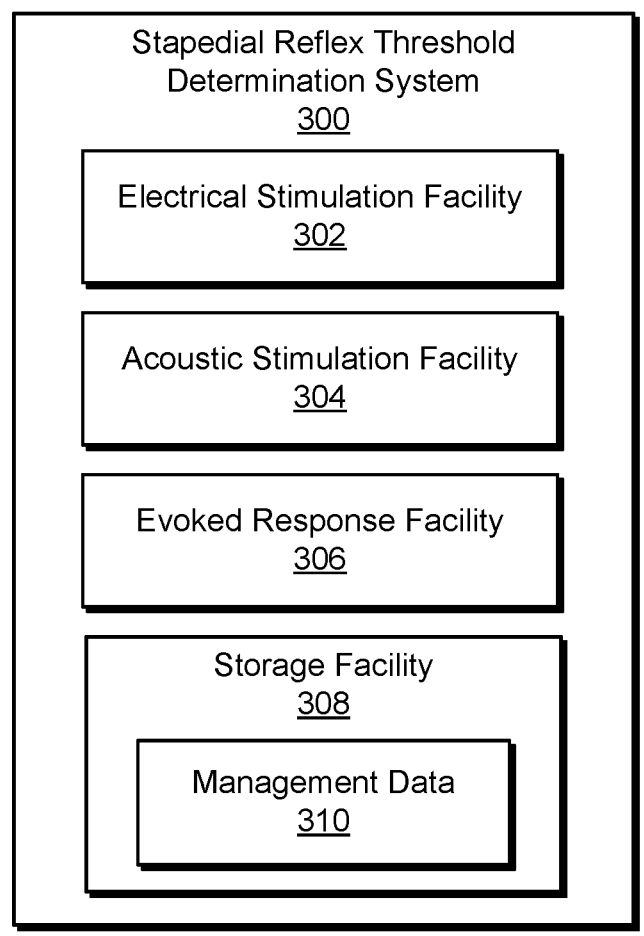
FIG. 3 illustrates exemplary components of an SRT determination system for determining an SRT based on electro-acoustic stimulation according to principles described herein.

FIG. 3 illustrates exemplary components of an SRT determination system 300 ("system 300") for determining an SRT based on electro-acoustic stimulation. As shown, system 300 may include, without limitation, an electrical stimulation facility 302, an acoustic stimulation facility 304, an evoked response facility 306, and a storage facility 308 selectively and communicatively coupled to one another. It will be recognized that although facilities 302 through 308 are shown to be separate facilities in FIG. 3, facilities 302 through 308 may be combined into fewer facilities, such as into a single facility, or divided into more facilities as may serve a particular implementation. Each of facilities 302 through 308 will now be described in more detail.

Electrical stimulation facility 302 may include one or more physical computing components (e.g., hardware and/or software components such as a processor, a memory, a communication interface, instructions stored on the memory for execution by the processor, etc.) that communicate with a cochlear implant coupled with system 300 to direct or facilitate directing the cochlear implant to apply electrical stimulation to a patient. For example, as will be described in more detail below, electrical stimulation facility 302 may direct the cochlear implant to apply electrical stimulation at a plurality of escalating electrical stimulation levels. Eventually, electrical stimulation facility 302 may direct the cochlear implant to apply electrical stimulation at a particular electrical stimulation level at which system 300 may detect that a stapedius reflex has been triggered and, as a result, may determine the SRT of the patient based on the particular electrical stimulation level.

Acoustic stimulation facility 304 may similarly include one or more physical computing components (e.g., hardware and/or software components separate from those of electrical stimulation facility 302 or shared with electrical stimulation facility 302) that communicate with a loudspeaker coupled with system 300 to direct or facilitate directing the loudspeaker to apply acoustic stimulation to the patient. For example, as will be described in more detail below, acoustic stimulation facility 304 may direct the loudspeaker to apply acoustic stimulation at a baseline acoustic stimulation level too low to trigger a stapedius reflex within the patient, but high enough to elicit an evoked response within the patient. For example, the evoked response that occurs within the patient in response to the acoustic stimulation applied to the patient at the baseline acoustic stimulation level may be an electrocochleographic ("ECoG") evoked potential or another suitable acoustically evoked potential. For example, as used herein, an "evoked response" may refer to any of an ECoG evoked potential, an auditory brainstem response ("ABR"), a intracochlear hair-cell response (i.e., cochlear microphonics), an auditory nerve response, a compound action potential, and/or any other type of neural or physiological response (other than a stapedius reflex) that may occur within a patient in response to application of acoustic stimulation to the patient. In some examples, evoked responses may originate from neural tissues, hair cell to neural synapses, inner or outer hair cells, or other sources.

Electrical stimulation facility 302 and acoustic stimulation facility 304 may work in conjunction with one another to apply what is referred to herein as an "electro-acoustic stimulation event" to the patient. An electro-acoustic stimulation event may include both electrical stimulation applied by the cochlear implant (e.g., as directed by electrical stimulation facility 302) as well as acoustic stimulation applied by the loudspeaker (e.g., as directed by acoustic stimulation facility 304). Examples of electro-acoustic stimulation events, including various timing relationships that may be employed with respect to the electrical stimulation and the acoustic stimulation included within the electro-acoustic stimulation events, will be described and illustrated in more detail below.

Unlike the gradually escalating electrical stimulation levels applied by the cochlear implant (i.e., as directed by electrical stimulation facility 302), acoustic stimulation facility 304 may consistently direct the loudspeaker to apply the acoustic stimulation at a consistent acoustic stimulation level (e.g., the baseline acoustic stimulation level). As such, and as will be further described and illustrated below, an evoked response that occurs in response to the application of the acoustic stimulation may be expected to have a consistent baseline evoked response level corresponding with the baseline acoustic stimulation level until the electrical stimulation is applied at a sufficiently high electrical stimulation level (i.e., the particular electrical stimulation level described above) that the stapedius reflex of the patient is triggered. At this point, the evoked response that occurs in response to the application of the acoustic stimulation may be significantly lower than the baseline evoked response level (e.g., at least a predetermined threshold amount lower) as a result of an effect of the triggered stapedius reflex, even though the acoustic stimulation level at which the acoustic stimulation is applied may be the same as usual (i.e., the baseline acoustic stimulation level).

To this end, evoked response facility 306 may include one or more physical computing components (e.g., hardware and/or software components separate from those implementing facilities 302 and/or 304 or components shared with facilities 302 and/or 304) that perform various operations in conjunction with the application of the electro-acoustic stimulation events to the patient performed by facilities 302 and 304. For example, evoked response facility 306 may identify the baseline evoked response level (e.g., from a baseline evoked response that occurs within the patient in response to acoustic stimulation being applied at the baseline acoustic stimulation level as directed by acoustic stimulation facility 304). After an electro-acoustic stimulation event has been applied to the patient (e.g., by facilities 302 and 304), evoked response facility 306 may further determine an evoked response level of an evoked response that occurs within the patient in response to the acoustic stimulation applied to the patient as part of the electro-acoustic stimulation event, and may detect that the stapedius reflex within the patient is triggered. For example, evoked response facility 306 may detect that the stapedius reflex is triggered by determining that the evoked response level of the evoked response is at least a predetermined threshold amount lower than the baseline evoked response level. Then, in response to the detection that the stapedius reflex within the patient is triggered, evoked response facility 306 may determine the SRT of the patient based on the particular electrical stimulation level at which the electrical stimulation included within the electro-acoustic stimulation event was applied by electrical stimulation facility 302.

Based on the determined SRT of the patient, system 300 (e.g., by way of the one or more physical computing components included within any of facilities 302 through 308 or in another facility not explicitly shown in FIG. 3) may determine an MCL of the patient. For example, because the MCL is known to be highly correlated with the SRT in most patients, system 300 may determine that the MCL is the same as the SRT, or an offset above or below the MCL. Once the MCL has been determined, system 300 may further provide data representative of the MCL of the patient to facilitate fitting the cochlear implant to the patient. For example, the MCL may be provided, by way of a cochlear implant system programming device or the like, to a clinician fitting the patient during a clinical fitting session. As mentioned above, it may be particularly advantageous for system 300 to determine the MCL and provide data representative of the MCL to facilitate the fitting of a cochlear implant to a patient who is unable to provide subjective feedback during the fitting (e.g., disabled patients, pediatric patients, etc.).

Storage facility 308 may maintain management data 310 and/or any other data received, generated, managed, maintained, used, and/or transmitted by facilities 302 through 306 in a particular implementation. Management data 310 may include data representative of electrical stimulation levels and/or acoustic stimulation levels that have been applied and/or are to be applied under direction of facilities 302 and/or 304, including a baseline acoustic stimulation level, a plurality of escalating electrical stimulation levels, and the like. Moreover, management data 310 may include SRTs, MCLs, evoked response data such as a baseline evoked response level, a predetermined threshold to indicate when a measured evoked response level is indicative of a stapedius reflex being triggered, historical evoked response levels that have been measured, and so forth. Management data 310 may further include any other data as may serve a particular implementation of system 300 to facilitate performing one or more of the operations described herein.

System 300 may include, be implemented as a part of, or be otherwise associated with a cochlear implant system (e.g., such as cochlear implant system 100 described above) in any of various ways as may serve various implementations. For example, in some implementations, cochlear implant system 100 may be implemented as an EAS system and system 300 may be implemented as (e.g., included within) a sound processor of the EAS system.

Alternatively, cochlear implant system 100 (e.g., whether implemented as an EAS system or as a standard cochlear implant system without a loudspeaker) may be communicatively coupled with a separate device that implements (e.g., includes) system 300. For example, system 300 may be implemented within a programming device used by a clinician to fit cochlear implants to patients. The programming device may, for instance, be communicatively coupled with a cochlear implant implanted within a patient by way of a sound processor included within cochlear implant system 100, and may be communicatively coupled directly with a loudspeaker. As another example, system 300 may be implemented by a mobile device (e.g., a smartphone, tablet computing device, or the like), a personal computer, or another device that includes or is communicatively coupled to a suitable loudspeaker (e.g., an earphone, a built-in speaker, a wireless speaker, etc.) and that is configured to communicate with the cochlear implant of cochlear implant system 100 (e.g., by way of the sound processor).

Figure 4:
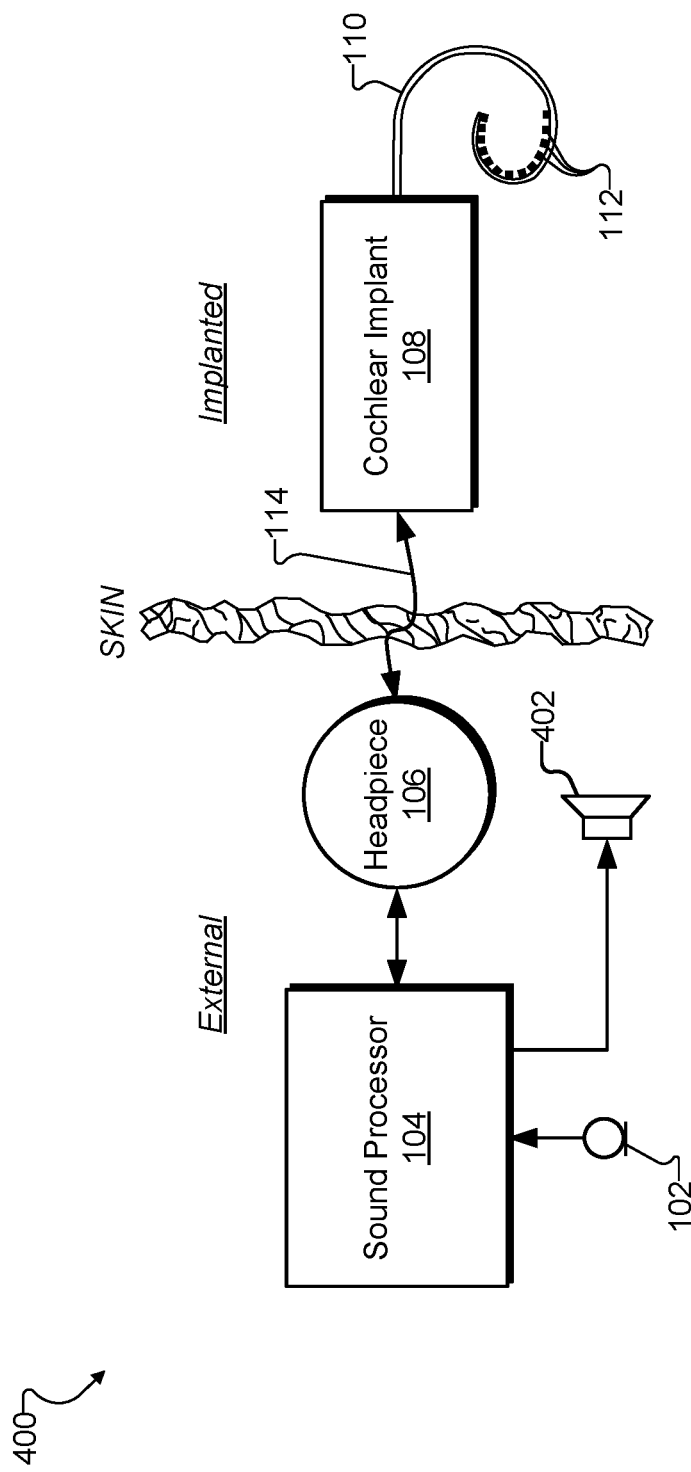
FIGS. 4-5 illustrate exemplary implementations of the SRT determination system of FIG. 3 that determine an SRT based on electro-acoustic stimulation according to principles described herein.
Figure 5:
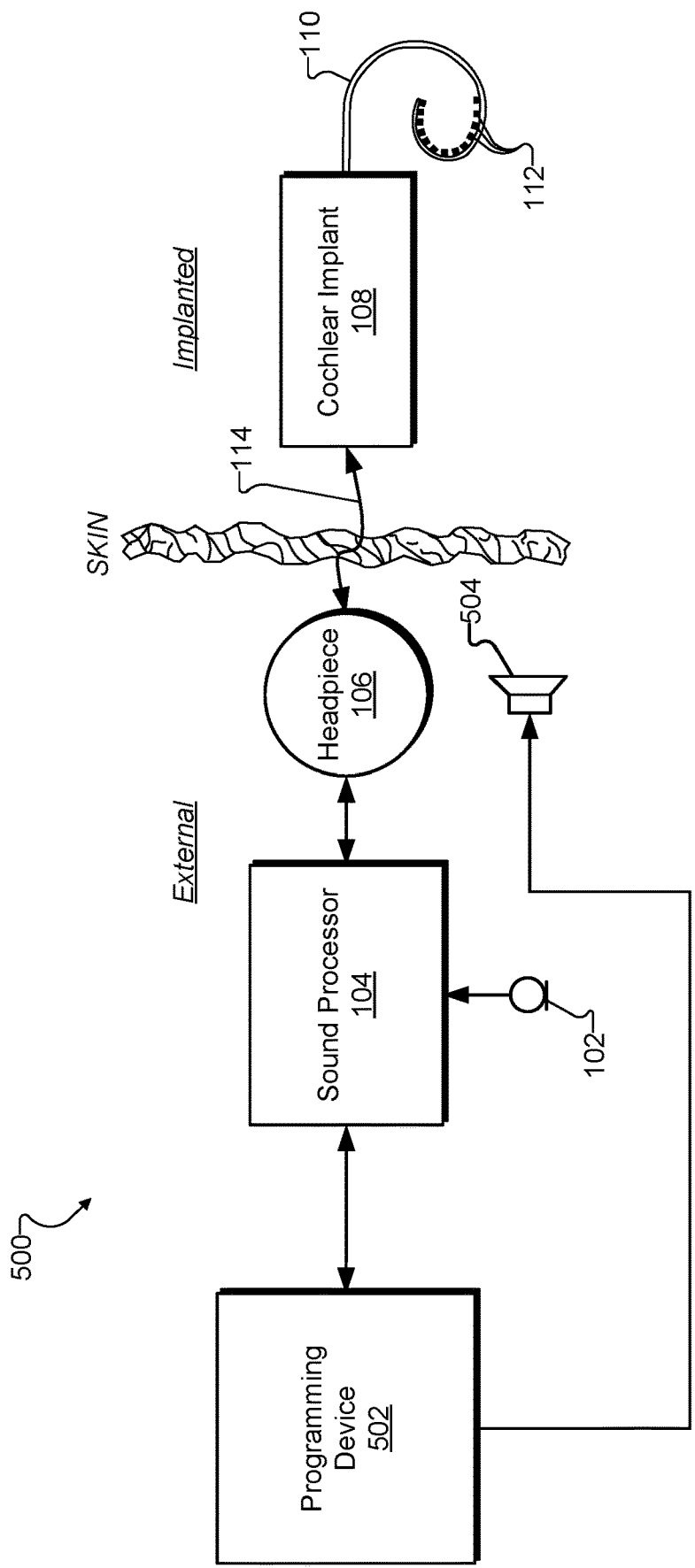

To illustrate, FIGS. 4-5 show exemplary implementations of system 300 in different configurations. For example, FIG. 4 illustrates an exemplary configuration 400 in which cochlear implant system 100 is implemented as an EAS system. As shown, the EAS system includes the same components as illustrated for cochlear implant system 100 in FIG. 1, except that the EAS system of FIG. 4 further includes a loudspeaker 402 communicatively coupled with sound processor 104. As such, system 300 may be implemented within sound processor 104. Sound processor 104 may direct an electro-acoustic stimulation event to be applied to a patient associated with the EAS system by, for example, directing (e.g., by way of headpiece 106 and communication link 114) cochlear implant 108 to apply electrical stimulation to the patient at an electrical stimulation level (e.g., one of the plurality of escalating electrical stimulation levels), and directing loudspeaker 402 to apply acoustic stimulation to the patient at an acoustic stimulation level (e.g., the baseline acoustic stimulation level).

More particularly, in certain examples, sound processor 104 may direct cochlear implant 108 to apply electrical stimulation at the electrical stimulation level by way of one or more electrodes 112 included in the plurality of electrodes implanted within the patient and coupled with the cochlear implant (e.g., included on lead 110). One or more of electrodes 112 in the plurality of electrodes on lead 110 may also be directed to detect an evoked response that occurs in response to, for example, the acoustic stimulation applied by loudspeaker 402. For instance, in some implementations, the same electrode 112 or electrodes 112 may be used both to apply the electrical stimulation to the patient and to detect the evoked response, while, in other implementations, a certain electrode (or electrodes) 112 may be used to apply the electrical stimulation to the patient that is different from the electrode (or electrodes) 112 used to detect the evoked response. In any case, the plurality of implanted electrodes 112 on lead 110 may be sufficient to determine the SRT based on electro-acoustic stimulation in accordance with the systems and methods described herein. In other words, no additional electrodes (i.e., other than electrodes 112) or other instrumentation implanted within the patient may be needed to facilitate the determination of the SRT based on the electro-acoustic stimulation.

As another example, FIG. 5 shows an exemplary configuration 500 in which cochlear implant system 100 is implemented as a standard cochlear implant system (i.e., without the dedicated loudspeaker 402 of the EAS system of configuration 400). As shown, configuration 500 includes the same components as illustrated for cochlear implant system 100 in FIG. 1, except that cochlear implant system 100 is communicatively coupled with a programming device 502, which is, in turn, communicatively coupled with a loudspeaker 504. In this example, system 300 may be implemented by (e.g., included within) programming device 502 separate from cochlear implant system 100 rather than (or in addition to) being implemented within sound processor 104.

Programming device 502 may be implemented by any suitable device used by, for example, a clinician or a patient to fit cochlear implant system 100 to the patient or otherwise set or alter configuration settings for cochlear implant system 100. For example, programming device 502 may be implemented as a clinician's programming interface ("CPI") device, as a general purpose mobile device (e.g., smartphone, tablet computing device, etc.), or as any other type of programming device as may serve a particular implementation. Programming device 502 may direct an electro-acoustic stimulation event to be applied to the patient associated with cochlear implant system 100 by, for example, directing (e.g., by way of sound processor 104, headpiece 106, and communication link 114) cochlear implant 108 to apply electrical stimulation to the patient at an electrical stimulation level (e.g., one of the plurality of escalating electrical stimulation levels), and directing loudspeaker 504 to apply acoustic stimulation to the patient at an acoustic stimulation level (e.g., the baseline acoustic stimulation level). For example, programming device 502 may direct cochlear implant 108 to apply the electrical stimulation at the electrical stimulation level by way of one or more of electrodes 112, any of which, as described above, may also be used to detect an evoked response to be analyzed by system 300 (i.e., by programming device 502 in this example).

Figure 6:
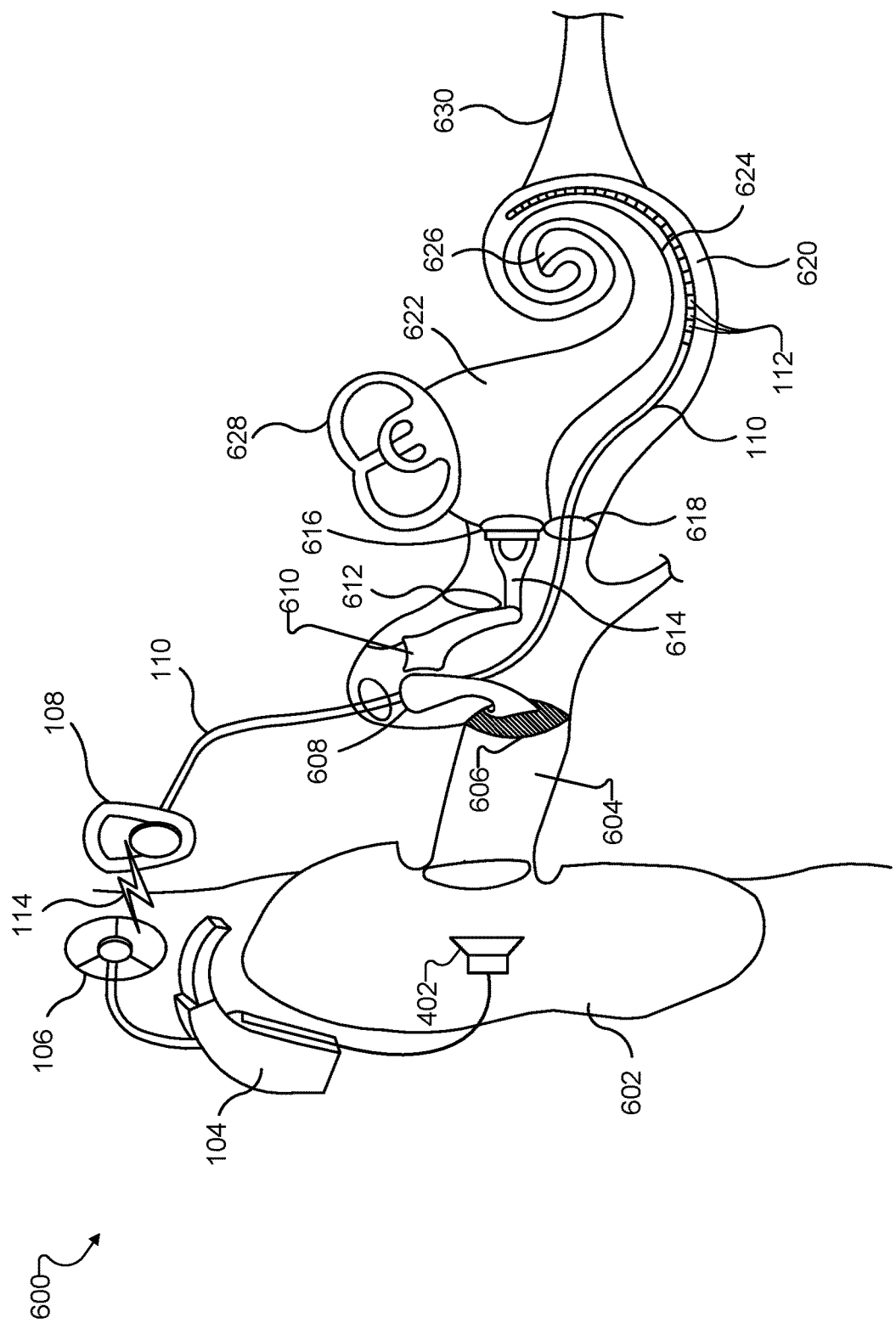
FIG. 6 illustrates a cross-sectional view of an exemplary implementation of the SRT determination system of FIG. 3 and the cochlear implant system of FIG. 1 integrated with and implanted within a patient according to principles described herein.

FIG. 6 illustrates a cross-sectional view of an exemplary implementation 600 of system 300 and cochlear implant system 100 integrated with and implanted within a patient. FIG. 6 also shows various anatomical features of the patient that are associated with the perception of sound.

As shown in FIG. 6, the ear of the patient may include or be associated with a pinna 602, an ear canal 604, a tympanic membrane 606 (also known as an eardrum membrane), a malleus 608 (also known as a hammer), an incus 610 (also known as an anvil), a stapedius muscle 612, a stapes 614 (also known as a stirrup), an oval window 616, and a round window 618. FIG. 6 further illustrates various structures included within the cochlea including, for example, a scala tympani 620, a scala vestibuli 622, a basilar membrane 624, and a helicotrema 626. Additional features such as a labyrinth 628 and an auditory nerve 630 are also shown.

In a normally functioning ear, tympanic membrane 606 may vibrate in response to sound that reaches tympanic membrane 606 through ear canal 604. For example, tympanic membrane 606 may vibrate in response to ambient sound generated externally to the patient's ear, or in response to sound (i.e., acoustic stimulation) applied by a loudspeaker communicatively coupled to an SRT determination system such as system 300. To illustrate, for instance, FIG. 6 shows that loudspeaker 402 is coupled to a behind-the-ear sound processor 104, which may implement system 300 as described above in relation to FIG. 4. While not explicitly illustrated in FIG. 6, it will also be understood that a loudspeaker coupled with a programming device (e.g., loudspeaker 504 coupled with programming device 502) could replace loudspeaker 402 in FIG. 4 to perform an analogous function, as described above in relation to FIG. 5.

Acoustic stimulation vibrating tympanic membrane 606 may be transferred to oval window 616 via the ossicular chain, which includes malleus 608, incus 610, and stapes 614. As described above, stapedius muscle 612 may involuntarily contract in response to uncomfortable or dangerously loud sounds in order to trigger a built-in hearing protection mechanism known as the stapedius reflex. To this end, stapedius muscle 612 may dampen hearing by exerting a force on stapes 614 to increase the impedance of the middle ear when such loud sound levels are detected. The damping caused by contraction of the stapedius muscle 612 may be on the order of approximately 20 dB, causing the loud sound levels to be perceived as being significantly less loud than they would otherwise be perceived to be. As a result, and as will be illustrated and discussed below, an evoked response that occurs in response to acoustic stimulation applied at a baseline acoustic stimulation level may have an evoked response level that is significantly reduced when the stapedius reflex is triggered (i.e., and the impedance of the middle ear is temporarily increased to protect the patient from loud sounds) as compared to when the stapedius reflex is not triggered.

As shown in FIG. 6, sound processor 104 may be located external to the user and mounted behind the ear (i.e., behind pinna 602). Headpiece 106 may be positioned such that a coil disposed therein may be inductively coupled to a corresponding coil included within cochlear implant 108. In this manner, sound processor 104 may transmit control parameters to cochlear implant 108 by way of communication link 114. Lead 110 may also be implanted within the patient such that electrodes 112 are disposed within the cochlea. Cochlear implant 108 may generate and apply electrical stimulation to one or more stimulation sites within the cochlea via electrodes 112.

As described above, system 300 may be coupled with a loudspeaker (e.g., one of loudspeakers 402 and 504) and with a cochlear implant (e.g., cochlear implant 108) and may perform operations to determine an SRT based on electro-acoustic stimulation. More particularly, system 300 may 1) identify a baseline evoked response level of a baseline evoked response that occurs within the patient in response to acoustic stimulation being applied by the loudspeaker to the patient at a baseline acoustic stimulation level too low to trigger a stapedius reflex within the patient, 2) direct the cochlear implant and the loudspeaker to apply an electro-acoustic stimulation event (e.g., including electrical stimulation applied by the cochlear implant at a particular electrical stimulation level and acoustic stimulation applied by the loudspeaker at the baseline acoustic stimulation level) to the patient, 3) determine an evoked response level of an evoked response that occurs within the patient in response to the acoustic stimulation applied to the patient as part of the electro-acoustic stimulation event, 4) detect that the stapedius reflex within the patient is triggered by determining that the evoked response level of the evoked response is at least a predetermined threshold amount lower than the baseline evoked response level, and 5) determine (e.g., in response to the detection that the stapedius reflex within the patient is triggered) a stapedius reflex threshold of the patient based on the particular electrical stimulation level.

To illustrate, FIGS. 7-10 show various exemplary waveforms illustrating various aspects and implementations of how these operations may be performed by an SRT determination system such as system 300 to determine the SRT of a patient based on electro-acoustic stimulation.

FIG. 7 illustrates exemplary waveforms 700 depicting an evoked response that occurs within a patient in response to acoustic stimulation being applied to the patient. More specifically, waveforms 700 illustrate one way that system 300 may identify the baseline evoked response level described above. That is, without doing anything to trigger the stapedius reflex (e.g., without directing the cochlear implant to apply electrical stimulation that could trigger the stapedius reflex), system 300 may direct the loudspeaker to apply test acoustic stimulation 702 to the patient at a baseline acoustic stimulation level 704 that meets particular criteria such as being too low to trigger the stapedius reflex within the patient, yet being high enough to cause a test evoked response 706 to occur within the patient.

Test acoustic stimulation 702 may be any acoustic stimulation (e.g., sound) as may serve a particular implementation. For example, test acoustic stimulation 702 may be a tone or other type of acoustic stimulation that is easy to control and hear at various acoustic stimulation levels. Baseline acoustic stimulation level 704 may be a predefined acoustic stimulation level that meets the above-mentioned criteria for substantially all patients, or that is at least known to meet these criteria for the patient being tested. For example, baseline acoustic stimulation level 704 may be approximately 80 decibels sound pressure level ("dB SPL"), approximately 100 dB SPL, or another suitable acoustic stimulation level too low to trigger the stapedius reflex but high enough to cause the evoked response to occur.

In association with (e.g., concurrently with or near in time to) directing test acoustic stimulation 702 to be applied, system 300 may also detect test evoked response 706 as test evoked response 706 occurs within the patient in response to the application of test acoustic stimulation 702. For example, system 300 may detect test evoked response 706 by way of one or more electrodes communicatively coupled to the cochlear implant that is coupled with system 300. As shown, test evoked response 706 may be characterized by a baseline evoked response level 708. Baseline evoked response level 708 may be expected to consistently characterize evoked responses that occur in response to an application of acoustic stimulation at baseline acoustic stimulation level 704 (e.g., such as evoked response 706) when a stapedius reflex is not triggered. Accordingly, system 300 may designate the baseline evoked response level expected for typical evoked responses as the baseline evoked response level 708 measured from test evoked response 706. For example, system 300 may designate the baseline evoked response level by storing baseline evoked response level 708 in storage facility 308 to be used for future comparisons without having to remeasure the baseline evoked response level more often than necessary.

In other examples, system 300 may identify the baseline evoked response level in other suitable ways as may serve other particular implementations. For example, if a suitable baseline evoked response level has already been stored (e.g., within storage facility 308), system 300 may identify the baseline evoked response level by loading the baseline evoked response level from storage. By using this method, system 300 may save time from having to measure the baseline evoked response level according to the method described in relation to FIG. 7 more often than necessary. In other examples, system 300 may identify the baseline evoked response level by receiving data representative of the baseline evoked response level from another system (e.g., from another component of cochlear implant system 100, from a lookup table accessed from a server or other system coupled with system 300 by way of a network connection, etc.), or in any other way as may serve a particular implementation.

Once system 300 has identified the baseline evoked response level, system 300 may apply various electro-acoustic stimulation events each including acoustic stimulation applied at the baseline acoustic stimulation level and electrical stimulation applied at escalating electrical stimulation levels until it is detected that an evoked response is lower than the baseline evoked response level by a threshold that indicates that the electrical stimulation triggered the stapedius reflex. In other words, prior to the application of the electro-acoustic stimulation event that includes electrical stimulation at the particular electrical stimulation level that triggers the stapedius reflex, system 300 may direct the cochlear implant and the loudspeaker to apply one or more additional electro-acoustic stimulation events to the patient. Each of the one or more additional electro-acoustic stimulation events may include electrical stimulation applied by the cochlear implant at a respective electrical stimulation level within a plurality of escalating electrical stimulation levels less than the particular electrical stimulation level, and acoustic stimulation applied by the loudspeaker at the baseline acoustic stimulation level. System 300 may determine one or more additional evoked response levels of one or more additional evoked responses that occur within the patient in response to the acoustic stimulation applied to the patient as part of the one or more additional electro-acoustic stimulation events. Additionally, system 300 may detect, for each of the respective electrical stimulation levels within the plurality of escalating electrical stimulation levels less than the particular electrical stimulation level, that the stapedius reflex within the patient is not triggered by determining that each of the one or more additional evoked response levels of the one or more additional evoked responses is within the predetermined threshold amount of the baseline evoked response level.

To illustrate, FIG. 8 illustrates exemplary waveforms 800 depicting an electro-acoustic stimulation event that system 300 applies to the patient that does not ultimately trigger the stapedius reflex or allow system 300 to determine the SRT. One or more electro-acoustic stimulation events such as that depicted in FIG. 8 may therefore be required to gradually build up the electrical stimulation level until reaching the particular electrical stimulation level that triggers the stapedius reflex (as will be illustrated below in FIG. 9). FIG. 8 also shows a respective evoked response that occurs within the patient in response to acoustic stimulation included within the electro-acoustic stimulation event of waveforms 800.

As shown, waveforms 800 in FIG. 8 include electrical stimulation 802 that is applied at an electrical stimulation level 804 that, as will be shown, happens to be too small to trigger the stapedius reflex. Electrical stimulation 802 may be applied by a cochlear implant (e.g., under direction of system 300 and by way of one or more electrodes communicatively coupled to the cochlear implant) for a first time period 806 of a first predetermined duration. Waveforms 800 further include, after a second time period 808 of a second predetermined duration, acoustic stimulation 810 applied at the same baseline acoustic stimulation level described above (i.e., baseline acoustic stimulation level 704, which should elicit an evoked response having baseline evoked response level 708 unless the stapedius reflex is triggered). Acoustic stimulation 810 may be applied by a loudspeaker (e.g., under direction of system 300) for a third time period 812 of a third predetermined duration. Additionally, at some point after the loudspeaker has begun applying acoustic stimulation 810, waveforms 800 show that system 300 detects an evoked response 814 at baseline evoked response level 708.

Because evoked response 814 is at baseline evoked response level 708, and because evoked response 814 occurred within a fourth time period 816 of when electrical stimulation 802 ceased (e.g., a time period short enough that the stapedius reflex would still be triggered if the stapedius reflex had been triggered by electrical stimulation 802), system 300 may determine that the stapedius reflex has not been triggered. For instance, system 300 may determine that electrical stimulation level 804 is still too low to trigger the stapedius reflex and, as a result, the SRT has not yet been determined and a different electrical stimulation level (e.g., an electrical stimulation level within the plurality of escalating electrical stimulation levels that is slightly higher than electrical stimulation level 804) should be tried next.

Collectively, electrical stimulation 802 and acoustic stimulation 810 may be an example of what is referred to herein as electro-acoustic stimulation or an electro-acoustic stimulation event due to a close relationship in space and time between electrical stimulation 802 and acoustic stimulation 810. For example, the cochlear implant that applies electrical stimulation 802 and the loudspeaker that applies acoustic stimulation 810 may both be associated with a same particular ear of the patient. Additionally, system 300 may direct the cochlear implant and the loudspeaker to apply electrical stimulation 802 and acoustic stimulation 810 ipsilaterally (e.g., with respect to the particular ear of the patient) in accordance with a predetermined timing relationship.

The predetermined timing relationship between electrical stimulation and acoustic stimulation applied as part of an electro-acoustic stimulation event may take any of various suitable forms. For example, as illustrated in FIG. 8, system 300 may direct the cochlear implant and the loudspeaker to apply the electro-acoustic stimulation event in accordance with the predetermined timing relationship by first directing (e.g., during first time period 806) the cochlear implant to apply electrical stimulation 802 while directing the loudspeaker to abstain from applying acoustic stimulation, then directing (e.g., during second time period 808) both the cochlear implant and the loudspeaker to abstain from applying stimulation immediately subsequent to first time period 806, and then directing (e.g., during third time period 812) the cochlear implant to abstain from applying electrical stimulation while directing the loudspeaker to apply acoustic stimulation 810 immediately subsequent to second time period 808.

As a numeric example, for instance, system 300 may apply an electro-acoustic stimulation event by directing the cochlear implant to apply electrical stimulation 802 for approximately 100 ms (first time period 806), followed by an approximately 10 ms pause (second time period 808), followed by directing the loudspeaker to apply acoustic stimulation 810 (e.g., a tone burst) for approximately 50 ms (third time period 812). At some point after acoustic stimulation 810 begins and within a few hundred milliseconds that it takes for a triggered stapedius reflex to relax again (i.e., longer than fourth time period 814), evoked response 814 may be detected and the evoked response level (i.e., baseline evoked response level 708 in this case) may be determined.

As described above, system 300 may direct the cochlear implant and the loudspeaker to periodically (e.g., approximately every few hundred milliseconds or so) apply an electro-acoustic stimulation event. For example, a first electro-acoustic stimulation event may be applied with a relatively low electrical stimulation level known to be too low to trigger the stapedius reflex, and each electro-acoustic stimulation event thereafter may incorporate electrical stimulation with gradually escalating electrical stimulation levels until a particular electrical stimulation level is reached that triggers the stapedius reflex. To determine that the particular electrical stimulation level has been reached, and to thereby determine the SRT, system 300 may rely on evoked responses that occur in response to the acoustic stimulation of each electro-acoustic stimulation event and the baseline evoked response level identified as described above in relation to FIG. 7.

To illustrate, FIG. 9, shows exemplary waveforms 900 depicting an electro-acoustic stimulation event that system 300 applies to the patient that does trigger the stapedius reflex and thereby allows system 300 to determine the SRT. For example, waveforms 900 may represent the final electro-acoustic stimulation event that is applied by system 300 after several other electro-acoustic stimulation events have been applied, and that allows system 300 to successfully accomplish the goal of determining the SRT of the patient. FIG. 9 also shows a respective evoked response that occurs within the patient in response to acoustic stimulation included within the electro-acoustic stimulation event of waveforms 900.

As shown, waveforms 900 in FIG. 9 include electrical stimulation 902 that is applied at an electrical stimulation level 904 that, as will be shown, happens to be large enough to trigger the stapedius reflex. Like electrical stimulation 802 and any other applications of electrical stimulation that were applied as part of other electro-acoustic stimulation events leading up to this electro-acoustic stimulation event, electrical stimulation 902 may be applied by a cochlear implant (e.g., under direction of system 300 and by way of one or more electrodes communicatively coupled to the cochlear implant) for first time period 806. Waveforms 900 further include, after second time period 808, acoustic stimulation 906 applied, again, at baseline acoustic stimulation level 704. As with acoustic stimulation 810 and any other applications of acoustic stimulation applied as part of other electro-acoustic stimulation events leading up to this electro-acoustic stimulation event, acoustic stimulation 906 may be applied by a loudspeaker (e.g., under direction of system 300) for third time period 812. Additionally, at some point after the loudspeaker has begun applying acoustic stimulation 906, waveforms 800 show that system 300 detects an evoked response 908 at an evoked response level 910 that is at least a predetermined threshold amount 912 lower than baseline evoked response level 708.

Because evoked response level 910 of evoked response 908 is at least the predetermined threshold amount 912 lower than baseline evoked response level 708, and because evoked response 908 occurred within fourth time period 816 of when electrical stimulation 902 ceased, system 300 may determine that the stapedius reflex has been triggered. For instance, system 300 may determine that electrical stimulation level 904 is just high enough to trigger the stapedius reflex and, as a result, may determine the SRT of the patient based on electrical stimulation level 904. For example, system 300 may determine that the SRT is the same as electrical stimulation level 904 or is within a predetermined offset (e.g., above or below) electrical stimulation level 904. Additionally, based on the SRT of the patient, system 300 may determine an MCL of the patient and provide data representative of the MCL of the patient to facilitate fitting the cochlear implant to the patient.

A specific numerical example associated with waveforms 800 and 900 will now be described. It will be understood that the specific numbers given in the example are arbitrary and are for illustrative purposes only, and that any of various suitable numbers may be used in various implementations. For purposes of the following example, it may be assumed that the patient has an SRT of approximately 200 clinical units ("CU").

Referring to the electro-acoustic stimulation event of FIG. 8, system 300 may first direct the cochlear implant to apply electrical stimulation 802 at 100 CU for 100 ms. Then, after a 10 ms pause, system 300 may direct the loudspeaker to apply acoustic stimulation 810 as a 500 Hz tone at 100 dB SPL (the baseline acoustic stimulation level) for 50 ms while also using one of the electrodes communicatively coupled to the cochlear implant (e.g., the same or a different electrode used to apply electrical stimulation 802) to monitor for an evoked response. System 300 may detect evoked response 814 and determine that the evoked response level of evoked response 814 is approximately equal to (e.g., not at least the predetermined threshold amount lower than) 50 microvolts COI which may be the baseline evoked threshold level that has been identified. As such, system 300 may determine that the SRT of the patient is greater than 100 CU and may thus begin this process again (e.g., after a pause for 50 ms or so). On the second round, electrical stimulation 802 may be increased to, for example, 105 CU and applied for 100 ms. After the 10 ms pause, the same 500 Hz tone may again be applied at the same 100 dB SPL baseline acoustic stimulation level for 50 ms while evoked responses are monitored. This time, evoked response 814 may again be approximately equal to the 50 μV baseline evoked threshold level. This process may continue as the electrical stimulation level is increased to 110 CU, 115 CU, 120 CU, etc., and each time the evoked response may still have the 50 μV baseline evoked threshold level.

Finally, referring to the electro-acoustic stimulation event illustrated in FIG. 9, when the process is repeated with electrical stimulation applied at 200 CU (and acoustic stimulation still applied at 100 dB SPL), evoked response 908 may be determined to be only, for example, 40 μV, rather than the usual 50 μV baseline evoked threshold level. In other words, if the predetermined threshold amount is 5 μV, it may be determined that the 40 μV evoked response level of evoked response 908 is at least 5 μV lower than the 50 μV baseline evoked response level (i.e., 10 μV lower). As such, system 300 may determine that the stapedius reflex was triggered by the 200 CU electrical stimulation, and that the SRT of the patient is approximately equal to 200 CU.

As described above, system 300 may direct the cochlear implant and the loudspeaker to apply electrical stimulation 802 and acoustic stimulation 810 ipsilaterally (e.g., with respect to one particular ear of the patient) in accordance with a predetermined timing relationship. The timing illustrated in waveforms 800 and 900 of FIGS. 8 and 9 illustrate a sequential-type predetermined timing relationship between electrical stimulation and acoustic stimulation applied as part of an electro-acoustic stimulation event.

To illustrate a concurrent-type predetermined timing relationship, FIG. 10 shows waveforms 1000 in which two electro-acoustic stimulation events are shown, a first electro-acoustic stimulation event where the stapedius reflex is not triggered and a second electro-acoustic stimulation event where the stapedius reflex is triggered. In the electro-acoustic stimulation events of FIG. 10, electrical stimulation and acoustic stimulation are applied concurrently. As with FIGS. 8 and 9, FIG. 10 also shows a respective evoked response that occurs within the patient in response to acoustic stimulation included within each electro-acoustic stimulation event of waveforms 1000.

Specifically, as shown, waveforms 1000 in FIG. 10 include electrical stimulation 1002-1 (of the first electro-acoustic stimulation event) and electrical stimulation 1002-2 (of the second electro-acoustic stimulation event) that are applied, respectively, at electrical stimulation level 804 (i.e., which is too low to trigger the stapedius reflex) and electrical stimulation level 904 (i.e., which is high enough to trigger the stapedius reflex). In certain examples, electrical stimulation 1002-1 and 1002-2 may each be applied by a cochlear implant (e.g., under direction of system 300 and by way of one or more electrodes communicatively coupled to the cochlear implant) for a first time period 1006 of a first predetermined duration. Waveforms 1000 further include acoustic stimulation 1008-1 (of the first electro-acoustic stimulation event) and acoustic stimulation 1008-2 (of the second electro-acoustic stimulation event), which are each applied at the same baseline acoustic stimulation level described above (i.e., baseline acoustic stimulation level 704, which may be expected to elicit an evoked response having baseline evoked response level 708 unless the stapedius reflex is triggered). As shown, acoustic stimulation 1008-1 may be applied by a loudspeaker (e.g., under direction of system 300) concurrently with electrical stimulation 1002-1, while acoustic stimulation 1008-2 may be applied by the loudspeaker concurrently with electrical stimulation 1002-2.

As used herein, electrical and acoustic stimulation are applied "concurrently" when at least part of a particular stimulation application (e.g., part of electrical stimulation 1002-1) overlaps or is applied simultaneously with at least part of another particular stimulation application (e.g., part of acoustic stimulation 1008-1), regardless of whether the entirety of both stimulation applications overlap or are applied simultaneously. Thus, for instance, both acoustic stimulation 1008-1 and 1008-2 may be applied for a second time period 1010 of a third predetermined duration, which may be different than first time period 1006. However, even though electrical stimulation 1002-1 and acoustic stimulation 1008-1 do not fully overlap, they may be considered to be concurrent since they at least partially overlap.

Additionally, at some point after the loudspeaker has begun applying acoustic stimulation 1008-1 (for the first electro-acoustic stimulation event) and acoustic stimulation 1008-2 (for the second electro-acoustic stimulation event), waveforms 1000 show that system 300 detects an evoked response 1012-1 at baseline evoked response level 708 for the first electro-acoustic stimulation event, and an evoked response 1012-2 at evoked response level 910 (i.e., at least predetermined threshold amount 912 less than baseline evoked response level 708) for the second electro-acoustic stimulation event.

Because evoked response 1012-1 is at baseline evoked response level 708, system 300 may determine that the stapedius reflex has not been triggered. For instance, system 300 may determine that electrical stimulation level 1002-1 is too low to trigger the stapedius reflex. However, because evoked response level 910 of evoked response 1012-2 is at least predetermined threshold amount 912 less than baseline evoked response level 708, system 300 may determine the stapedius reflex has been triggered. As a result, upon detecting evoked response 1012-2, system 300 may determine the SRT of the patient based on electrical stimulation level 904, as described above in relation to FIG. 9.

FIG. 11 illustrates an exemplary method 1100 for determining an SRT based on electro-acoustic stimulation according to principles described herein. One or more of the operations shown in FIG. 11 may be performed by SRT determination system 300 and/or any implementation thereof. While FIG. 11 illustrates exemplary operations according to one embodiment, other embodiments may omit, add to, reorder, and/or modify any of the operations shown in FIG. 11.

In operation 1102, an SRT determination system communicatively coupled with a cochlear implant implanted within a patient having residual hearing and with a loudspeaker associated with the patient may identify a baseline evoked response level of a baseline evoked response. For example, the baseline evoked response may occur within the patient in response to acoustic stimulation being applied by the loudspeaker to the patient at a baseline acoustic stimulation level too low to trigger a stapedius reflex within the patient. Operation 1102 may be performed in any of the ways described herein.

In operation 1104, the SRT determination system may direct the cochlear implant and the loudspeaker to apply an electro-acoustic stimulation event to the patient. For example, the electro-acoustic stimulation event may include electrical stimulation applied by the cochlear implant at a particular electrical stimulation level. The electro-acoustic stimulation event may further include acoustic stimulation applied by the loudspeaker at the baseline acoustic stimulation level. Operation 1104 may be performed in any of the ways described herein.

In operation 1106, the SRT determination system may determine an evoked response level of an evoked response that occurs within the patient in response to the acoustic stimulation applied to the patient as part of the electro-acoustic stimulation event. Operation 1106 may be performed in any of the ways described herein.

In operation 1108, the SRT determination system may detect that the stapedius reflex within the patient is triggered. Operation 1108 may be performed in any of the ways described herein. For example, operation 1108 may be performed by determining that the evoked response level of the evoked response is at least a predetermined threshold amount lower than the baseline evoked response level.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
 a loudspeaker associated with a patient having residual hearing;
 a cochlear implant implanted within the patient; and
 a stapedius reflex threshold determination system communicatively coupled with the loudspeaker and the cochlear implant, and that
  identifies a baseline evoked response level of a baseline evoked response that occurs within the patient in response to acoustic stimulation being applied by the loudspeaker to the patient at a baseline acoustic stimulation level too low to trigger a stapedius reflex within the patient,
  directs the cochlear implant and the loudspeaker to apply a first electro-acoustic stimulation event to the patient, the first electro-acoustic stimulation event including first electrical stimulation applied at a level less than a particular electrical stimulation level and first acoustic stimulation applied at the baseline acoustic stimulation level,
  determines a first evoked response level of a first evoked response that occurs within the patient in response to the first acoustic stimulation included in the first electro-acoustic stimulation event,
  detects that the stapedius reflex is not triggered by determining that the first evoked response level of the first evoked response is within a predetermined threshold amount of the baseline evoked response level,
  directs the cochlear implant and the loudspeaker to apply a second electro-acoustic stimulation event to the patient, the second electro-acoustic stimulation event including second electrical stimulation and second acoustic stimulation applied in accordance with a predetermined timing relationship between the second electrical stimulation and the second acoustic stimulation, the second electrical stimulation applied by the cochlear implant at the particular electrical stimulation level and the second acoustic stimulation applied by the loudspeaker at the baseline acoustic stimulation level,
  determines a second evoked response level of a second evoked response that occurs within the patient in response to the second acoustic stimulation included in the second electro-acoustic stimulation event, and
  detects that the stapedius reflex within the patient is triggered by determining that the second evoked response level of the second evoked response is at least the predetermined threshold amount lower than the baseline evoked response level.

2. The system of claim 1, wherein the stapedius reflex threshold determination system further:
 determines, based on the particular electrical stimulation level and in response to the detection that the stapedius reflex within the patient is triggered, a stapedius reflex threshold of the patient;
 determines, based on the determined stapedius reflex threshold of the patient, a most comfortable level of the patient; and
 provides data representative of the most comfortable level of the patient to facilitate fitting the cochlear implant to the patient.

3. The system of claim 1, wherein the first and second evoked responses that occur within the patient in response to the first and second acoustic stimulation included respectively in the first and second electro-acoustic stimulation events are electrocochleographic evoked potentials.

4. The system of claim 1, wherein:
the cochlear implant and the loudspeaker are both associated with a same particular ear of the patient; and
the stapedius reflex threshold determination system directs the cochlear implant and the loudspeaker to apply the first and second electro-acoustic stimulation events ipsilaterally with respect to the particular ear of the patient.

5. The system of claim 1, wherein the stapedius reflex threshold determination system directs the cochlear implant and the loudspeaker to apply the second electro-acoustic stimulation event in accordance with the predetermined timing relationship by:
directing, during a first time period of a first predetermined duration, the cochlear implant to apply the second electrical stimulation and the loudspeaker to abstain from applying acoustic stimulation;
directing, during a second time period of a second predetermined duration and immediately subsequent to the first time period, the cochlear implant to abstain from applying electrical stimulation and the loudspeaker to abstain from applying acoustic stimulation; and
directing, during a third time period of a third predetermined duration and immediately subsequent to the second time period, the cochlear implant to abstain from applying electrical stimulation and the loudspeaker to apply the second acoustic stimulation.

6. The system of claim 1, wherein the stapedius reflex threshold determination system directs the cochlear implant and the loudspeaker to apply the second electro-acoustic stimulation event in accordance with the predetermined timing relationship by:
directing, during a first time period of a first predetermined duration, the cochlear implant to apply the second electrical stimulation; and
directing, during a second time period of a second predetermined duration and that is at least partially concurrent with the first time period, the loudspeaker to apply the second acoustic stimulation.

7. The system of claim 1, wherein, prior to the application of the second electro-acoustic stimulation event, the stapedius reflex threshold determination system further:
directs the cochlear implant and the loudspeaker to apply one or more additional electro-acoustic stimulation events to the patient, each of the one or more additional electro-acoustic stimulation events including
additional electrical stimulation applied by the cochlear implant at a respective electrical stimulation level within a plurality of escalating electrical stimulation levels less than the particular electrical stimulation level, and
additional acoustic stimulation applied by the loudspeaker at the baseline acoustic stimulation level;
determines one or more additional evoked response levels of one or more additional evoked responses that occur within the patient in response to the additional acoustic stimulation applied to the patient as part of the one or more additional electro-acoustic stimulation events; and
detects, for each of the respective electrical stimulation levels within the plurality of escalating electrical stimulation levels less than the particular electrical stimulation level, that the stapedius reflex within the patient is not triggered by determining that each of the one or more additional evoked response levels of the one or more additional evoked responses is within the predetermined threshold amount of the baseline evoked response level.

8. The system of claim 1, wherein the stapedius reflex threshold determination system identifies the baseline evoked response level by:
directing the loudspeaker to apply test acoustic stimulation to the patient at the baseline acoustic stimulation level too low to trigger the stapedius reflex within the patient;
detecting a test evoked response that occurs within the patient in response to the application of the test acoustic stimulation; and
designating the baseline evoked response level as an evoked response level of the test evoked response that occurs within the patient in response to the application of the test acoustic stimulation.

9. The system of claim 1, wherein the baseline acoustic stimulation level is a predetermined acoustic stimulation level that is too low to trigger the stapedius reflex within the patient and high enough to cause the first and second evoked responses to occur within the patient.

10. The system of claim 1, wherein:
the system is implemented as an electro-acoustic stimulation system; and
the stapedius reflex threshold determination system is implemented as a sound processor included within the electro-acoustic stimulation system.

11. The system of claim 1, further comprising a cochlear implant system that includes the cochlear implant and a sound processor communicatively coupled with the cochlear implant;
wherein the stapedius reflex threshold determination system is implemented by a programming device separate from the cochlear implant system, the programming device communicatively coupled directly with the loudspeaker and communicatively coupled with the cochlear implant by way of the sound processor.

12. The system of claim 1, wherein:
the application of the second electrical stimulation at the particular electrical stimulation level is performed by way of one or more electrodes included in a plurality of electrodes implanted within the patient and coupled with the cochlear implant; and
the determination of the second evoked response level of the second evoked response includes detecting the second evoked response by way of one or more electrodes included in the plurality of electrodes implanted within the patient.

13. A sound processor communicatively coupled with a loudspeaker associated with a patient having residual hearing and with a cochlear implant implanted within the patient, the sound processor comprising:
at least one physical computing component that
identifies a baseline evoked response level of a baseline evoked response that occurs within the patient in response to acoustic stimulation being applied by the loudspeaker to the patient at a baseline acoustic stimulation level too low to trigger a stapedius reflex within the patient,
directs the cochlear implant and the loudspeaker to apply a first electro-acoustic stimulation event to the patient, the first electro-acoustic stimulation event including first electrical stimulation applied at a level less than a particular electrical stimulation level and first acoustic stimulation applied at the baseline acoustic stimulation level, determines a first evoked response level of a first evoked response that occurs within the patient in response to the first acoustic stimulation included in the first electro-acoustic stimulation event, detects that the stapedius reflex is not triggered by determining that the first evoked response level of the first evoked response is within a predetermined threshold amount of the baseline evoked response level, directs the cochlear implant and the loudspeaker to apply a second electro-acoustic stimulation event to the patient, the second electro-acoustic stimulation event including second electrical stimulation and second acoustic stimulation applied in accordance with a predetermined timing relationship between the second electrical stimulation and the second acoustic stimulation, the second electrical stimulation applied by the cochlear implant at the particular electrical stimulation level and the second acoustic stimulation applied by the loudspeaker at the baseline acoustic stimulation level, determines a second evoked response level of a second evoked response that occurs within the patient in response to the second acoustic stimulation included in the second electro-acoustic stimulation event, and detects that the stapedius reflex within the patient is triggered by determining that the second evoked response level of the second evoked response is at least the predetermined threshold amount lower than the baseline evoked response level.

14. The sound processor of claim 13, wherein the at least one physical computing component further:
determines, based on the particular electrical stimulation level and in response to the detection that the stapedius reflex within the patient is triggered, a stapedius reflex threshold of the patient;
determines, based on the determined stapedius reflex threshold of the patient, a most comfortable level of the patient; and
provides data representative of the most comfortable level of the patient to facilitate fitting the cochlear implant to the patient.

15. The sound processor of claim 13, wherein the first and second evoked responses that occur within the patient in response to the first and second acoustic stimulation included respectively in the first and second electro-acoustic stimulation events are electrocochleographic evoked potentials.

16. The sound processor of claim 13, wherein:
the cochlear implant and the loudspeaker are both associated with a same particular ear of the patient; and
the sound processor directs the cochlear implant and the loudspeaker to apply the first and second electro-acoustic stimulation events ipsilaterally with respect to the particular ear of the patient.

17. The sound processor of claim 13, wherein the sound processor directs the cochlear implant and the loudspeaker to apply the second electro-acoustic stimulation event in accordance with the predetermined timing relationship by:
directing, during a first time period of a first predetermined duration, the cochlear implant to apply the second electrical stimulation and the loudspeaker to abstain from applying acoustic stimulation;
directing, during a second time period of a second predetermined duration and immediately subsequent to the first time period, the cochlear implant to abstain from applying electrical stimulation and the loudspeaker to abstain from applying acoustic stimulation; and
directing, during a third time period of a third predetermined duration and immediately subsequent to the second time period, the cochlear implant to abstain from applying electrical stimulation and the loudspeaker to apply the second acoustic stimulation.

18. The sound processor of claim 13, wherein the sound processor directs the cochlear implant and the loudspeaker to apply the second electro-acoustic stimulation event in accordance with the predetermined timing relationship by:
directing, during a first time period of a first predetermined duration, the cochlear implant to apply the second electrical stimulation; and
directing, during a second time period of a second predetermined duration and that is at least partially concurrent with the first time period, the loudspeaker to apply the second acoustic stimulation.

19. A method comprising:
identifying, by a stapedius reflex threshold determination system communicatively coupled with a cochlear implant implanted within a patient having residual hearing and with a loudspeaker associated with the patient, a baseline evoked response level of a baseline evoked response that occurs within the patient in response to acoustic stimulation being applied by the loudspeaker to the patient at a baseline acoustic stimulation level too low to trigger a stapedius reflex within the patient;
directing, by the stapedius reflex threshold determination system, the cochlear implant and the loudspeaker to apply a first electro-acoustic stimulation event to the patient, the first electro-acoustic stimulation event including first electrical stimulation applied at a level less than a particular electrical stimulation level and first acoustic stimulation applied at the baseline acoustic stimulation level;
determining, by the stapedius reflex threshold determination system, a first evoked response level of a first evoked response that occurs within the patient in response to the first acoustic stimulation included in the first electro-acoustic stimulation event;
detecting, by the stapedius reflex threshold determination system, that the stapedius reflex is not triggered by determining that the first evoked response level of the first evoked response is within a predetermined threshold amount of the baseline evoked response level;
directing, by the stapedius reflex threshold determination system, the cochlear implant and the loudspeaker to apply a second electro-acoustic stimulation event to the patient, the second electro-acoustic stimulation event including second electrical stimulation and second acoustic stimulation applied in accordance with a predetermined timing relationship between the second electrical stimulation and the second acoustic stimulation, the second electrical stimulation applied by the cochlear implant at the particular electrical stimulation level and the second acoustic stimulation applied by the loudspeaker at the baseline acoustic stimulation level;
determining, by the stapedius reflex threshold determination system, a second evoked response level of a second evoked response that occurs within the patient in response to the second acoustic stimulation included in the second electro-acoustic stimulation event; and
detecting, by the stapedius reflex threshold determination system, that the stapedius reflex within the patient is triggered by determining that the second evoked response level of the second evoked response is at least the predetermined threshold amount lower than the baseline evoked response level.

20. The method of claim 19, further comprising:

determining, by the stapedius reflex threshold determination system and in response to the detection that the stapedius reflex within the patient is triggered, a stapedius reflex threshold of the patient based on the particular electrical stimulation level;

determining, by the stapedius reflex threshold determination system based on the determined stapedius reflex threshold of the patient, a most comfortable level of the patient; and providing, by the stapedius reflex threshold determination system, data representative of the most comfortable level of the patient to facilitate fitting the cochlear implant to the patient.

* * * * *